United States Patent
Cheng et al.

(10) Patent No.: US 6,861,163 B2
(45) Date of Patent: Mar. 1, 2005

(54) AROMATIC COMPOUNDS AND ORGANIC LIGHT EMITTING DIODES

(75) Inventors: Chien-Hong Cheng, Hsinchu (TW); Huai-Ting Shih, Hsinchu (TW); Kuo-Chen Wu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 10/417,252

(22) Filed: Apr. 17, 2003

(65) Prior Publication Data

US 2004/0076852 A1 Apr. 22, 2004

(30) Foreign Application Priority Data

Oct. 16, 2002 (TW) ........................................ 91123869 A

(51) Int. Cl.$^7$ ............................................. H05B 33/14
(52) U.S. Cl. ........................ 428/690; 428/917; 313/504; 313/506
(58) Field of Search ................................ 428/690, 917; 313/503, 504, 506

(56) References Cited

U.S. PATENT DOCUMENTS

| | | | | |
|---|---|---|---|---|
| 5,621,131 A | * | 4/1997 | Kreuder et al. | ................ 558/46 |
| 6,582,837 B1 | * | 6/2003 | Toguchi et al. | ............. 428/690 |
| 2002/0177009 A1 | * | 11/2002 | Suzuki et al. | ............... 428/690 |

* cited by examiner

Primary Examiner—Rena Dye
Assistant Examiner—Camie S Thompson
(74) Attorney, Agent, or Firm—Bacon & Thomas

(57) ABSTRACT

A blue organic light emitting diode (LED) comprises a cathode formed on a substrate, a light emitting layer formed on said cathode, and an anode formed on said light emitting layer, which is characterized in that said light emitting layer comprises a compound of the following formulas I or II: wherein $Ar_1$ and $Ar_2$ independently are substituted or unsubstituted isochrysenyl $$Ar_1—Ar_2 \qquad\qquad I$$

$$Ar_1—Ar_3—Ar_2 \qquad\qquad II$$

(triphenylenyl), anthracenyl, naphthalyl, biphenyl, pyrenyl, or phenanthrenyl; $Ar_3$ is substituted or unsubstituted phenylene, biphenylene, naphthylene, anthracenylene, or fluorenylene.

12 Claims, No Drawings

AROMATIC COMPOUNDS AND ORGANIC LIGHT EMITTING DIODES

BACKGROUND OF THE INVENTION

Researches on the organic LEDs started by Pope, et al. in 1963 (J. Chem. Phys. 38 (1963) 2042). They used anthracene as a monolithic light emitting material, which could emit blue light under a high voltage. Since then, despite of improvements carried out by a few researchers (Phys. Rev. Lett. 14 (1965) 229; Sol. State Comm. 32 (1979) 683; Thin Solid Films 94 (1982) 476), the operating voltage was still too high, and the efficiency of energy conversion was still too low, preventing such materials from being used for practical purposes.

In 1987, Tang, et al. (Appl. Phys. Lett., 51 (1987) 914) used a vapor deposition technique to produce an organic LED with a structure of ITO/Diamine/Alq$_3$/Mg:Ag, wherein ITO was a conductive transparent indium/tin oxide, and Alq$_3$ was tris(8-hydroxyquinoline) aluminum. Because such an organic LED had an external quantum efficiency of 1% and a high brightness of 1000 cd/m$^2$ (10V), researches and developments on the organic LEDs accelerate since then. Two years later, a research group in the Carvendish Laboratory of the Cambridge University in England used PPV as a light emitting material to make a LED having a structure of ITO/PPV/Ca, which emitted an olive color with a quantum efficiency of 0.05%, wherein ITO is a positive electrode, Ca is a negative electrode, and the PPV is poly(phenylene vinylene) (Nature, 347(1990) 539; U.S. Pat. Nos. 5,247,190 (1993); 5,425,125 (1995); 5,401,827 (1995)).

A primitive organic LED has a single organic layer, which is an organic light emitting layer disposed between a transparent electrode (as a positive electrode) and a metal electrode (as a negative electrode). In order to improve the light emitting efficiency of the organic LED, one LED can have two organic layers, wherein the first layer is a hole transporting layer and the second layer is the organic light emitting layer, or the first layer is the organic light emitting layer and the second layer is an electron transporting layer. Some LEDs may have three organic layers, which sequentially are the hole transporting layer, the organic light emitting layer, and the electron transporting layer. The light emitting process of such LEDs is described in the following: After the application of a positive bias, holes and electrons are separately emitted from the positive and the negative electrodes driven by an electric field resulting from the positive bias, which, after overcoming individual energy barriers, encounter each other in the light emitting layer and form excitons. The excitons rapidly decay radiantly back to the base state while emitting light. Such a LED is a type of Schottky characteristics.

Even though there are many blue LEDs have been proposed, only very few of them have a high brightness, excellent CIE coordinates, and a high efficiency. Among known OLED materials[1-6], Alq$_3$ was the most popular dopant for green and red OLEDs. However, the energy gap between HOMO and LUMO of Alq$_3$ is too small[7] such that Alq$_3$ is not suitable to be used as a blue dopant. Therefore, for the development of full color displays with blue, green and red light, it was crucial to find a blue emitter that is stable and reliable and has a high efficiency.[8]

References:

[1] a) Y.-H. Kim, D.-C. Shin, S.-H. Kim, C.-H. Ko, H.-S. Yu, Y.-S. Chae, S.-K. Kwon, Adv. Mater. 2001, 13, 1690. b) C. Hosokawa, H. Higashi, H. Nakamura, T. Kusumoto, Appl. Phys. Lett. 1995, 67, 3853. c) Z. Gao, C. S. Lee, I. Bello, S. T. Lee, R.-M. Chen, T.-Y. Luh, J. Shi, C. W. Tang, Appl. Phys. Lett. 1999, 74, 865. d) S.-F. Liu, Q. Wu, H. L. Schmider, H. Aziz, N.-X. Hu, Z. Popovic, S. Wang, J. Am. Chem. Soc. 2000, 122, 3671. e) Sakon, Y.; Ohnuma, T.; Hashimoto, M.; Saito, S.; Tsutsui, T.; Adachi, C. U.S. Pat. No. , 5,077,142, 1994. f) Hosakawa, C.; Sakamoto, S.; Kusumoto, T. U.S. Pat. No. 5,389,444, 1995.

[2] C. H. Chen, J. Shi, Coordination Chem. Rev. 1998, 171, 161.

[3] X. T. Tao, H. Suzuki, T. Wada, S. Miyata, H. Sasabe, J. Am. Chem. Soc. 1999, 121, 9447.

[4] a) Y. Liu, J. Guo, J. Feng, H. Zhang, Y. Li, Y. Wang, Appl. Phys. Lett. 2001, 78, 2300. b) N.-X. Hu, M. Esteghamatian, S. Xie, Z. Popovic, A.-M. Hor, B. Ong, S. Wang, Adv. Mater. 1999, 11, 1460.

[5] a) W.-B. Im, H.-K. Hwang, J.-G. Lee, K. Han, Y. Kim, Appl. Phys. Lett. 2001, 79, 1387. b) Y. Kim, J.-G. Lee, S. Kim, Adv. Mater. 1999, 11, 1463. c) C. Schmitz, H.-W. Schmidt, M. Thelakkat, Chem. Mater. 2000, 12, 3012.

[6] a) J, Pang, Y. Tao, S. Freiberg, X.-P. Yang, M. D'Iorio, S. Wang, J. Mater. Chem. 2002, 12, 206. b) Y. Geng, D. Katsis, S. W. Culligan, J. J. Ou, S. H. Chen, L. J. Rothberg, Chem. Mater. 2002, 14, 463. c) B. Z. Tang, X. Zhan, G. Yu, P. P. S. Lee, Y. Liu, D. Zhu, J. Mater. Chem. 2001, 11, 2974. d) J.-F. Morin, S. Beauprè, M. Leclerc, I. Lèvesque, M. D'Iorio, Appl. Phys. Lett. 2002, 80, 341. e) H. Kajii, T. Tsukagawa, H. Okuno, T. Taneda, K. Yoshino, Y. Ohmori, Thin Solid Films 2001, 393, 388. f) Q. Wu, J. A. Lavigne, Y. Tao, M. D'Iorio, S. Wang, Chem Mater. 2001, 13, 71. g) M. Matsuura, T. Kusumoto, H. Tokailin, U.S. Pat. No. 5,516,577, 1996.

[7] a) L. C. Picciolo, H. Murata, Z. H. Kafafi, Appl. Phys. Lett. 2001, 78, 2378. b) J. Shi, C. W. Tang, Appl. Phys. Lett. 1997, 70, 1665. c) F. Steuber, J. Staudigel, M. St össel, J. Simmerer, A. Winnacker, H. Spreitzer, F. Weissortel, J. Salbeck, Adv. Mater. 2000, 12, 130. d) C. W. Tang, S. A. VanSlyke, C. H. Chen, J. Appl. Phys. 1989, 65, 3610.

[8] a) Y. T. Tao, E. Balasubramanian, A. Danel, P. Tomasik, Appl. Phys. Lett. 2000, 77, 933. b) Y. T. Tao, E. Balasubramanian, A. Danel, B. Jarosz, P. Tomasik, Chem. Mater. 2001, 13, 1207. c) Y. Hamada, H. Kanno, T. Tsujioka, H. Takahashi, T. Usuki, Appl. Phys. Lett. 1999, 75, 1682. d) V. Bulović, A. Shoustikov, M. A. Baldo, E. Bose, V. G. Kozlov, M. E. Thompson, S. R. Forrest. Chem. Phys. Lett. 1998, 287, 455.

SUMMARY OF THE INVENTION

A primary objective of the present invention is to provide an organic compound that can be used as a light emitting layer and a hole transporting layer for a blue LED. A blue LED produced from such a material shows a high brightness, high external quantum and current efficiency, and excellent CIE coordinates.

The present invention relates to a bi-molecular aromatic compound with a main structure of formula (I):

wherein $Ar_1$ and $Ar_2$ are a same polypenyl or independently are different polyphenyls, e.g. isochrysenyl (triphenylenyl), anthracenyl, naphthalyl, biphenyl, pyrenyl, phenanthrenyl, etc., having one or more substituents of the following functional groups, e.g. alkyl, cyano, phenyl, halo, and methoxy, etc.

Furthermore, an aryl ($Ar_3$) is optionally inserted between the two polyphenyls, $Ar_1$ and $Ar_2$, so that the aromatic compound of the present invention has the following formula II:

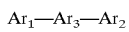

wherein $Ar_1$ and $Ar_2$ are defined as above; $Ar_3$ is selected from the group consisting of phenylene, biphenylene, naphthylene, anthracenylene, and fluorenylene, etc. $Ar_3$ may have one or more substituents of the following functional groups, e.g. alkyl, silyl, cyano, substituted or unsubstituted phenyl, and methoxy.

The present invention provides an organic light emitting diode, which comprises: a positive electrode formed on a substrate; a negative electrode; and a light emitting layer disposed between said positive electrode and said negative electrode, wherein said light emitting layer comprises a compound having the aforesaid formula I or II.

Preferably, the organic light emitting diode further comprises an electron transporting layer formed between said light emitting layer and said negative electrode. More preferably, said light emitting layer is also a hole transporting layer, or the organic light emitting diode further comprises a hole transporting layer formed between said positive electrode and said light emitting layer.

Preferably, the organic light emitting diode further comprises a hole injection modification layer formed between said positive electrode and said hole transporting layer.

Preferably, said light emitting layer is a compound having the formula I, and $Ar_1$ and $Ar_2$ are the same. More preferably, said compound having formula I is a compound having the following formula Ia-1 or Id-1:

Ia-1
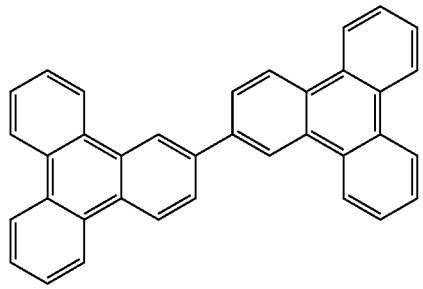

Id-1
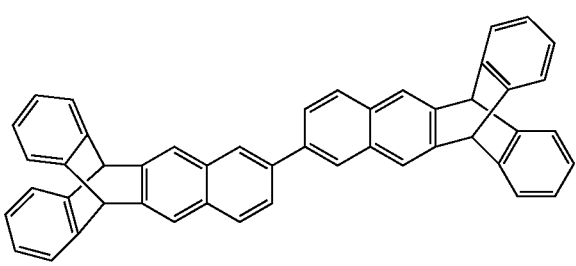

Preferably, said light emitting layer is a compound having the formula II, and $Ar_1$ and $Ar_2$ are the same, and more preferably, $Ar_3$ is phenylene. Most preferably, said compound having formula II is a compound having the following formula IIa-1 or IIb-1:

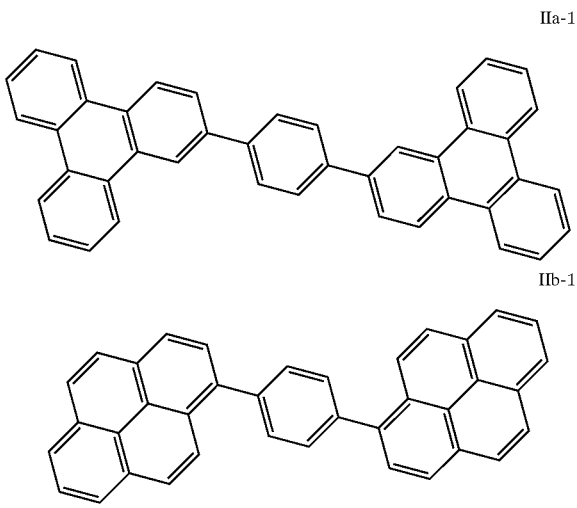

DETAILED DESCRIPTION OF THE INVENTION

The present invention will be further elaborated by the following preferred embodiments of the present invention, wherein (Ia)~(Ii) are examples of the compound I, (IIa)~(IIx) are examples of the compound II:

(Ia)
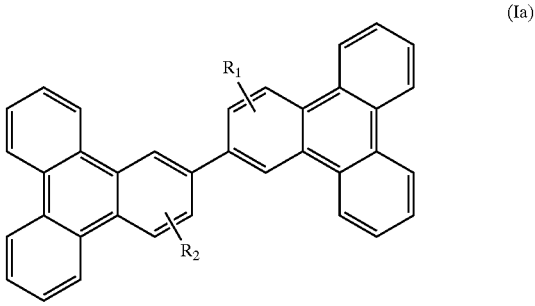

wherein $Ar_1=Ar_2=$isochrysenyl (triphenylenyl), $R_1$ and $R_2$ independently are hydrogen, C1–C6 alkyl, or cyano;

(Ib)
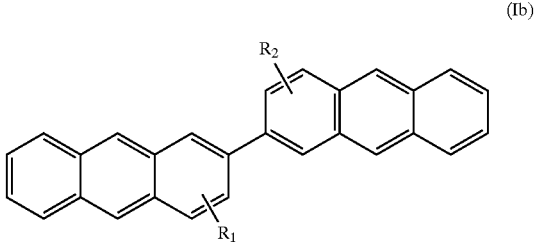

wherein Ar$_1$=Ar$_2$=anthracenyl, R$_1$ and R$_2$ independently are hydrogen, C1–C6 alkyl, or cyano;

(Ic)

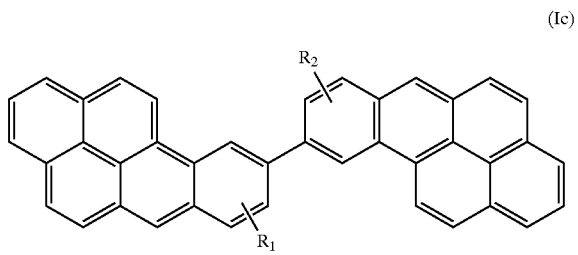

wherein Ar$_1$ and Ar$_2$ are identical aryl shown in the above, R$_1$ and R$_2$ independently are hydrogen, C1–C6 alkyl, or cyano;

(Id)

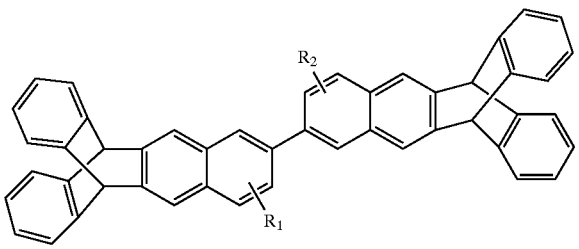

wherein Ar$_1$ and Ar$_2$ are identical aryl shown in the above, R$_1$ and R$_2$ independently are hydrogen, C1–C6 alkyl, or cyano;

(Ie)

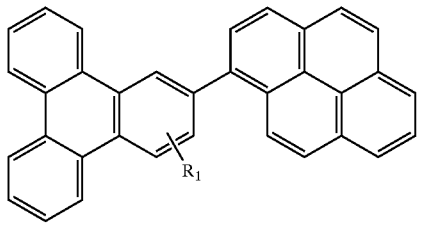

wherein Ar$_1$=isochrysenyl (triphenylenyl), Ar$_2$=pyrenyl, R$_1$ is hydrogen, C1–C6 alkyl, or cyano;

(If)

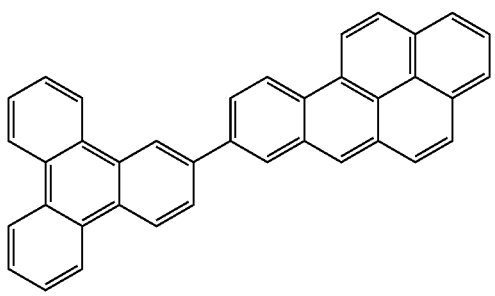

Ar$_1$=isochrysenyl (triphenylenyl), Ar$_2$ is an aryl shown in the above, (Ig)

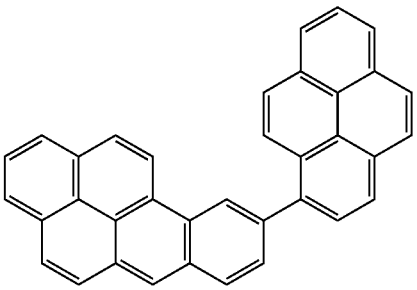

wherein Ar$_1$ is aryl shown in the above, and Ar$_2$=pyrenyl;

(Ih)

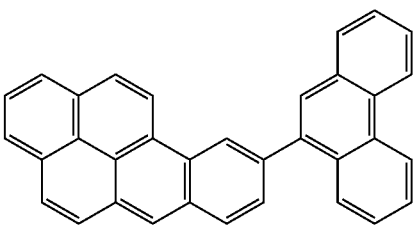

Ar$_1$ is an aryl with a structure shown in the above; Ar$_2$=phenanthrenyl;

(Ii)

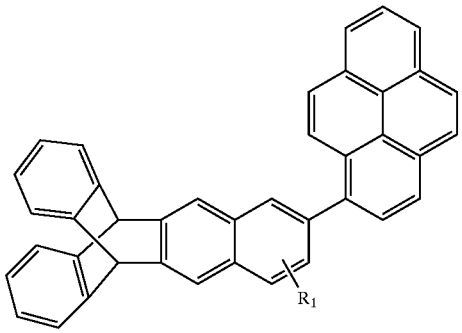

wherein Ar$_1$ is aryl with a structure shown in the above, Ar$_2$=pyrenyl, and R$_1$ is hydrogen, C1–C6 alkyl, or cyano;

(IIa)

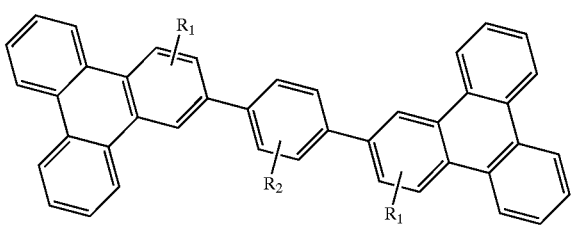

wherein Ar$_3$=phenylene, Ar$_1$=Ar$_2$=isochrysenyl (triphenylenyl), R$_1$ and R$_2$ independently are hydrogen, C1–C6 alkyl, or cyano;

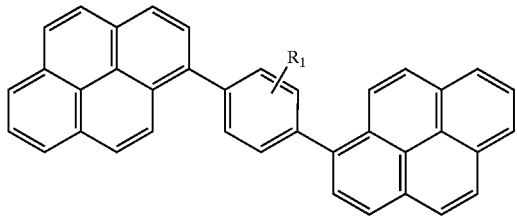
(IIb)

wherein Ar$_3$=phenylene, Ar$_1$=Ar$_2$=pyrenyl, R$_1$ is hydrogen, C1–C6 alkyl, or cyano;

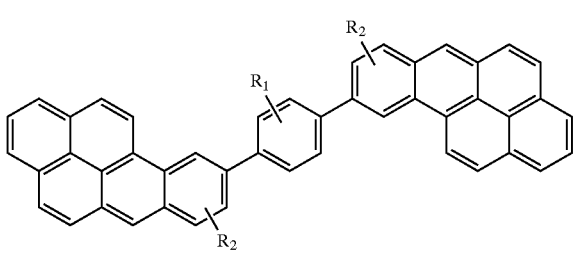
(IIc)

wherein Ar$_3$=phenylene, Ar$_1$ and Ar$_2$ are aryl with a structure shown in the above, R$_1$ and R$_2$ independently are hydrogen, C1–C6 alkyl, or cyano;

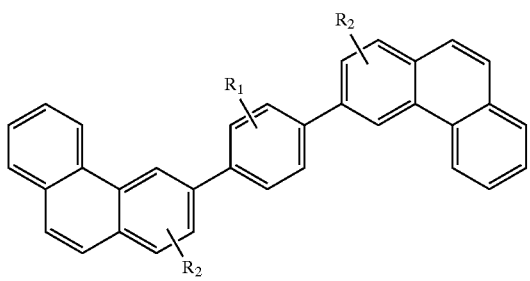
(IId)

wherein Ar$_3$=phenylene, Ar$_1$=Ar$_2$=phenanthrenyl, R$_1$ and R$_2$ independently are hydrogen, C1–C6 alkyl, or cyano;

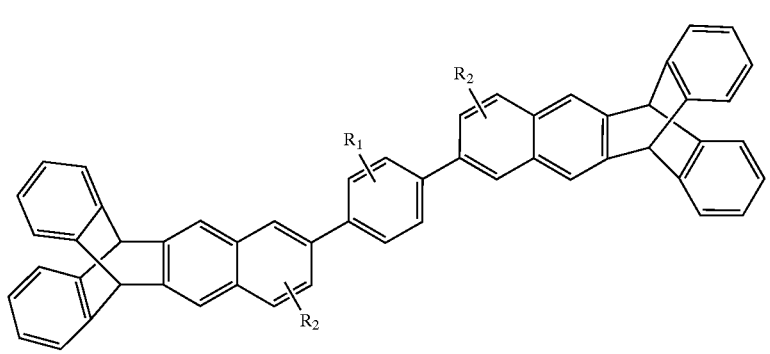
(IIe)

wherein Ar$_3$=phenylene, Ar$_1$ and Ar$_2$ are aryl with a structure shown in the above, R$_1$ and R$_2$ independently are hydrogen, C1–C6 alkyl, or cyano;

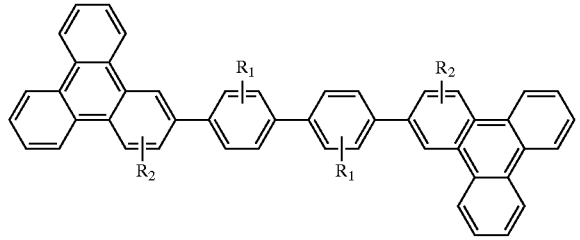
(IIf)

wherein Ar$_3$ biphenylene, Ar$_1$=Ar$_2$=isochrysenyl (triphenylenyl), R$_1$ and R$_2$ independently are hydrogen, C1–C6 alkyl, or cyano;

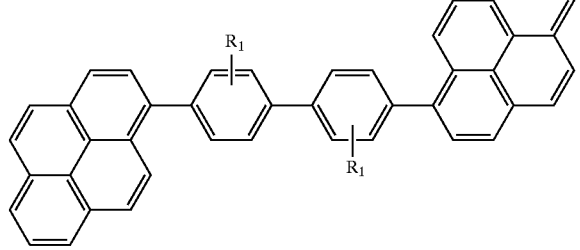
(IIg)

wherein Ar$_3$=biphenylene, Ar$_1$=Ar$_2$=pyrenyl, R$_1$ is hydrogen, C1–C6 alkyl, or cyano;

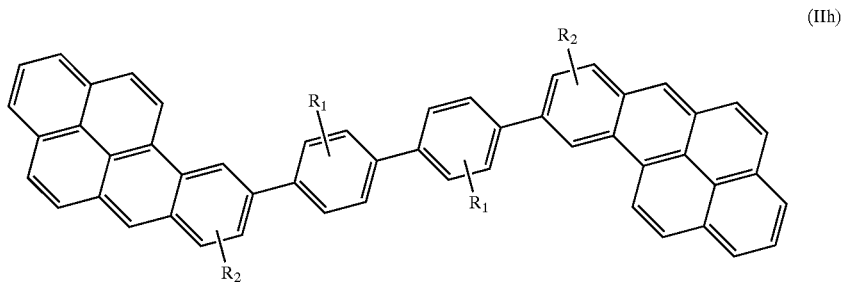

wherein Ar₃=biphenylene, Ar₁ and Ar₂ are aryl with a structure shown in the above, $R_1$ and $R_2$ independently are hydrogen, C1–C6 alkyl, or cyano;

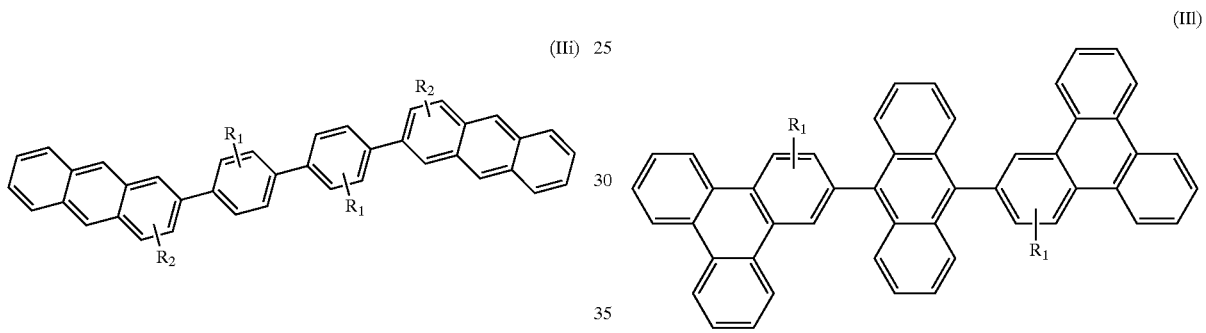

wherein Ar₃=biphenylene, Ar₁=Ar₂=anthracenyl, $R_1$ and $R_2$ independently are hydrogen, C1–C6 alkyl, or cyano;

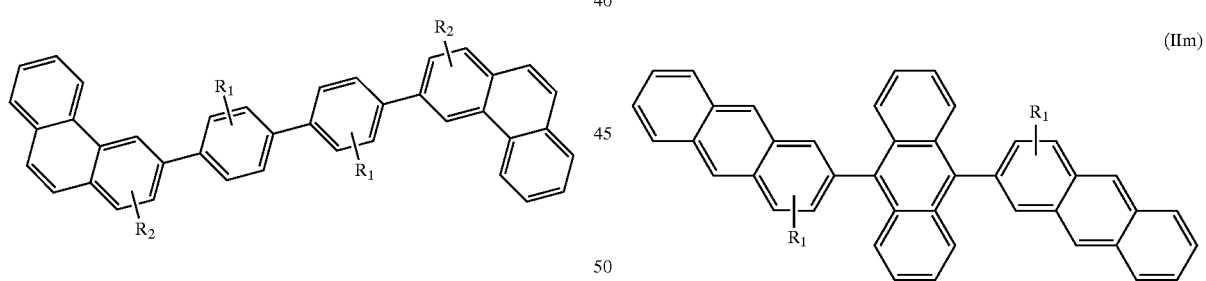

wherein Ar₃=biphenylene, Ar₁=Ar₂=phenanthrenyl, $R_1$ and $R_2$ independently are hydrogen, C1–C6 alkyl, or cyano;

wherein Ar₃=biphenylene, Ar₁ and Ar₂ are an aryl with a structure shown in the above, $R_1$ and $R_2$ independently are hydrogen, C1–C6 alkyl, or cyano;

wherein Ar₃=anthracenylene, Ar₁=Ar₂=isochrysenyl (triphenylenyl), $R_1$ is hydrogen, C1–C6 alkyl, or cyano;

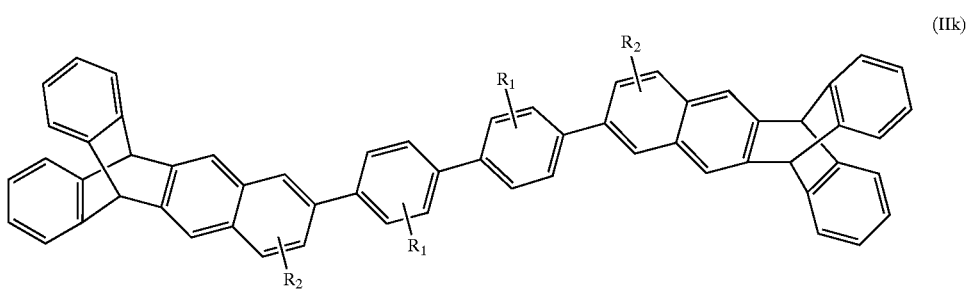

wherein Ar₃=anthracenylene, Ar₁=Ar₂=anthracenyl, R₁ is hydrogen, C1–C6 alkyl, or cyano;

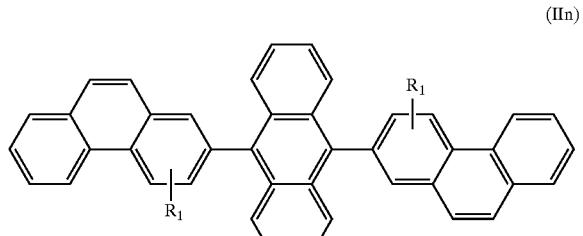
(IIn)

wherein Ar₃=anthracenylene, Ar₁=Ar₂=phenanthrenyl, R₁ is hydrogen, C1–C6 alkyl, or cyano;

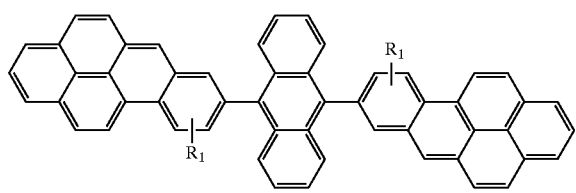
(IIo)

wherein Ar₃=anthracenylene, Ar₁ and Ar₂ are an aryl with a structure shown in the above, R₁ is hydrogen, C1–C6 alkyl, or cyano;

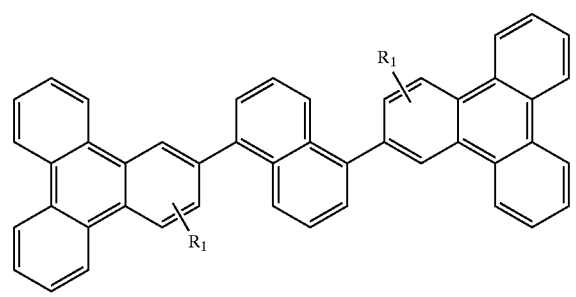
(IIp)

wherein Ar₃=naphthylene, Ar₁=Ar₂=isochrysenyl (triphenylenyl), R₁ is hydrogen, C1–C6 alkyl, or cyano;

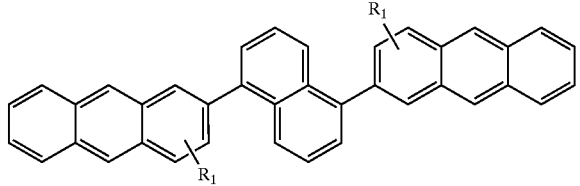
(IIq)

wherein Ar₃=naphthylene, Ar₁=Ar₂=anthracenyl, R₁ is hydrogen, C1–C6 alkyl, or cyano;

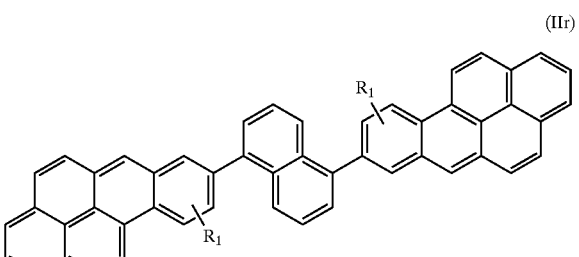
(IIr)

wherein Ar₃=naphthylene, Ar₁ and Ar₂ are aryl with a structure shown in the above, R₁ is hydrogen, C1–C6 alkyl, or cyano;

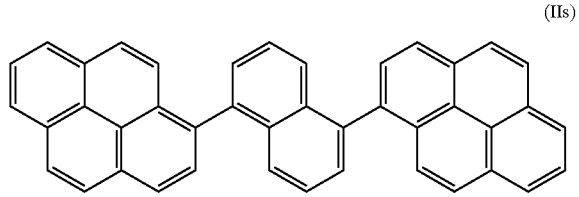
(IIs)

wherein Ar₃=naphthylene, and Ar₁=Ar₂=pyrenyl;

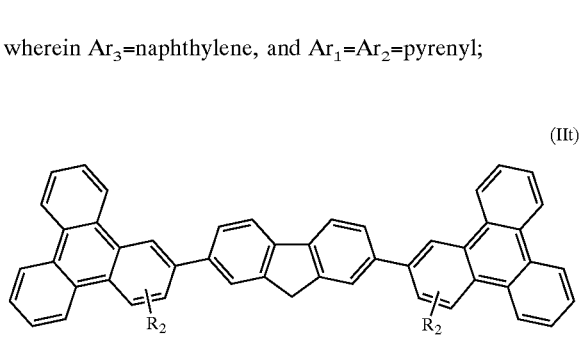
(IIt)

wherein Ar₃=fluorenylene, Ar₁=Ar₂=isochrysenyl (triphenylenyl), R₂ is hydrogen, C1–C6 alkyl, or cyano;

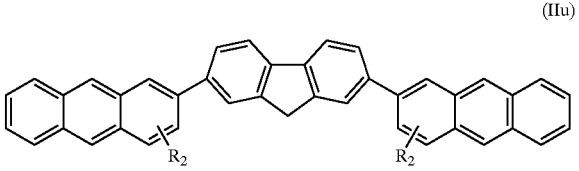
(IIu)

wherein Ar₃=fluorenylene, Ar₁=Ar₂=anthracenyl, R₂ is hydrogen, C1–C6 alkyl, or cyano;

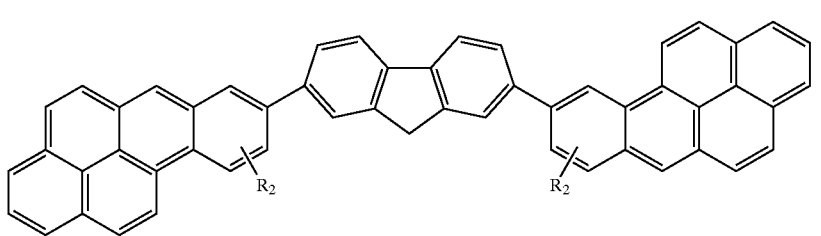
(IIv)

wherein Ar₃=fluorenylene, Ar₁ and Ar₂ are aryl with a structure shown in the above, $R_2$ is hydrogen, C1–C6 alkyl, or cyano;

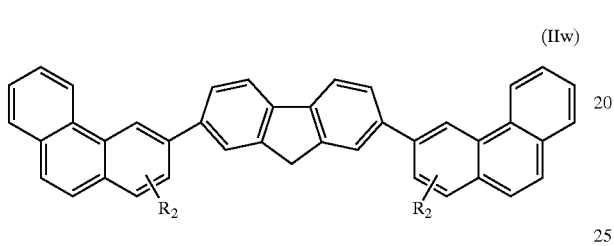
(IIw)

wherein Ar₃=fluorenylene, Ar₁=Ar₂=phenanthrenyl, $R_2$ is hydrogen, C1–C6 alkyl, or cyano;

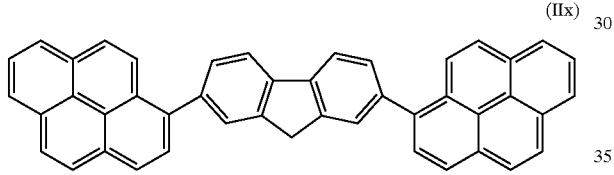
(IIx)

wherein Ar₃=fluorenylene, Ar₁=Ar₂=pyrenyl.

EXAMPLES

The present invention will be described in greater detail by the following examples.

The synthesis methods of the abovementioned materials were classified in the following: Ia, Ib, Ic, Id and derivatives thereof could be synthesized by a same method; Ie, If, Ig, Ih, Ii, IIa, IIc, IIe, IIf, IIh, IIi, IIj, IIk, IIl, IIm, IIn, IIo, IIp, IIq, IIr, IIt, IIu, IIv, IIw and derivatives thereof could be synthesized by a same method; and IIb, IIg, IIs, IIx and derivatives thereof could be synthesized by a same method.

The following examples synthesized Ia-1 ($R_1$=$R_2$=H; 2,2'-bitriphenylenyl), Ia-2 ($R_1$=$R_2$=CH₃; 4,4'-Dimethyl-[2,2']bitriphenylenyl), Id-1 ($R_1$=$R_2$=H), IIa-1 ($R_1$=$R_2$=H) and IIb-1 ($R_1$=H).

Compounds III to V of the following formulae were used in Example 1 to Example 5:

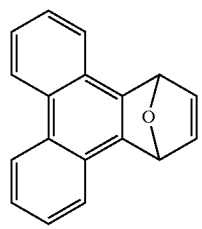
III

-continued

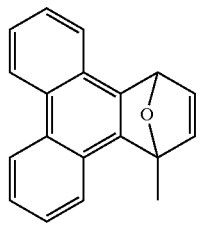
IV

V

Example 1

Synthesis of Ia-1 ($R_1$=$R_2$=H) 2,2'-Bitriphenylenyl)

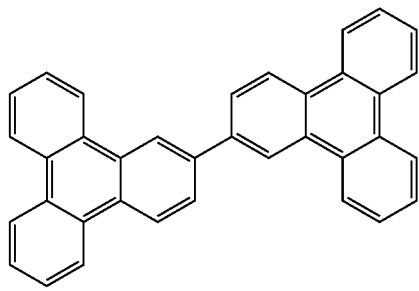
Ia-1

2.44 g (10 mmol) of III, 1.31 g (20.0 mmol) of zinc powder and 0.14 g (0.25 mmol) of Pd(dba)₂ were placed in a 250 ml two-necked reaction bottle. Vacuum was developed in the reaction bottle then nitrogen was introduced into the reaction bottle, and this cycle was repeated a few times. 40 ml of toluene was introduced into the reaction bottle, and the resulting mixture was mixed at room temperature for about 3 minutes. After the color of the solution had changed from purple to light yellow, the reaction bottle was placed in an ice water bath for cooling. 1.80 g (15.0 mmol) of trichlorosilane was dripped into the reaction bottle in about 30 seconds. Upon completion of the introduction of trichlorosilane, the reaction bottle was removed from the ice water bath, and the reaction mixture was stirred at room temperature for 6 hours. The reacted solution was filtered with silica gel and diatomite, and was washed with dichloromethane. The combined filtrate was concentrated on a rotary evaporator. The resulting solid was separated on a silica gel column by using a mixture of ethyl acetate and hexane as eluent (ethyl acetate:hexane=1:5). After separation, 1.81 g of a pale yellow product [Ia-1] was obtained with a yield of 80%. Mp.: 356° C. $^1$H NMR (400 MHz, CDCl$_3$): [ppm]: 9.06 (d, J=2 Hz, 2 H), 8.87–8.81 (m, 4 H), 8.75–8.70 (m, 6 H), 8.12 (dd, J=1.6, 8.4 Hz, 2 H), 7.74–7.70 (m, 8 H). $^{13}$C-NMR (125 MHz, CDCl$_3$): δ[ppm]: 139.88, 130.25, 130.12, 129.88, 129.81, 129.64, 129.12, 127.47, 127.38, 127.35, 126.62, 124.08, 123.45, 123.43, 123.40, 122.08. HRMS (EI$^+$): calculated value (C$_{36}$H$_{22}$): 454.1722, experimental value: ([M]$^+$) 454.1722.

Example 2

Synthesis of Ia-2 (R$_1$=R$_2$=CH$_3$)

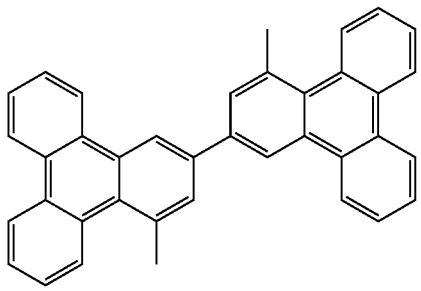

Ia-2

2.72 g (10 mmol) of IV, 1.31 g (20.0 mmol) of zinc powder and 0.14 g (0.25 mmol) of Pd(dba)$_2$ were placed in a 250 ml two-necked reaction bottle. Vacuum was developed in the reaction bottle then nitrogen was introduced into the reaction bottle, and this cycle was repeated a few times. 40 ml of toluene was introduced into the reaction bottle, and the resulting mixture was stirred at room temperature for about 3 minutes. After the color of the solution had changed from purple to yellow, the reaction bottle was cooled in an ice water bath. 1.80 g (15.0 mmol) of trichlorosilane was dripped into the reaction bottle in about 30 seconds. Upon completion of the introduction of trichlorosilane, the reaction bottle was removed from the ice water bath, and the reaction mixture was stirred at room temperature for 6 hours. The reacted solution was filtered with silica gel and diatomite, and was washed with dichloromethane. The combined filtrate was concentrated on a rotary evaporator, and the resulting solid product was purified by separation with a silica gel column. The eluent used a mixed solvent of ethyl acetate:hexane=1:5. After separation, a pale yellow solid product was obtained.

Example 3

Synthesis of Id-1 (R$_1$=R$_2$=H)

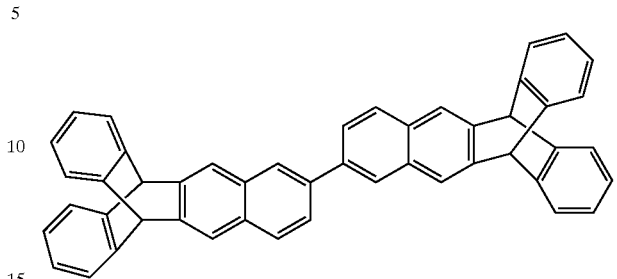

3.04 g (10 mmol) of V, 1.31 g (20.0 mmol) of zinc powder and 0.14 g (0.25 mmol) of Pd(dba)$_2$ were placed in a 250 ml two-necked reaction bottle. Vacuum was developed in the reaction bottle then nitrogen was introduced into the reaction bottle, and this cycle was repeated a few times. After the color of the solution had changed from purple to yellow, the reaction bottle was cooled in an ice water bath for temperature reduction. 1.80 g (15.0 mmol) of trichlorosilane was dripped into the reaction bottle in about 30 seconds. Upon completion of the introduction of trichlorosilane, the reaction bottle was removed from the ice water bath, and the reaction mixture was stirred at room temperature for 6 hours. The reacted solution was filtered with silica gel and diatomite, and was washed with dichloromethane. The combined filtrate was concentrated on a rotary evaporator, and the resulting solid product was purified by separation with a silica gel column. The eluent used was a mixed solvent of ethyl acetate:hexane=1:5.

Example 4

Synthesis of IIa-1 (R$_1$=R$_2$=H)

2.44 g (10 mmol) of III, 1.48 g (4.5 mmol) of p-diiodobenzene, 1.31 g

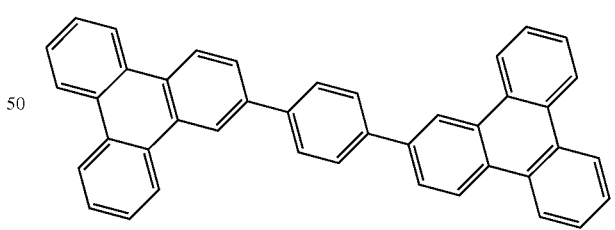

(20.0 mmol) of zinc powder and 0.14 g (0.25 mmol) of Pd(dba)$_2$ were placed in a 250 ml two-necked reaction bottle. 40 ml of toluene and 10 ml of triethylamine were introduced into the reaction bottle. Vacuum was developed in the reaction bottle then nitrogen was introduced into the reaction bottle, and this cycle was repeated a few times. The resulting mixture was stirred at room temperature for about 3 minutes, and then was heated under refluxing for 16 hours. The reacted solution was filtered with silica gel and diatomite, and was washed with dichloromethane. The combined filtrate was concentrated on a rotary evaporator, and the resulting solid product was purified by separation with a silica gel column. The eluent used was a mixed solvent of ethyl acetate:hexane=1:5. After separation, a pale yellow solid product IIa-1 was obtained.

Example 5

Synthesis of IIb-1 ($R_1$=H), 1,4-bipyrenylbenzene:

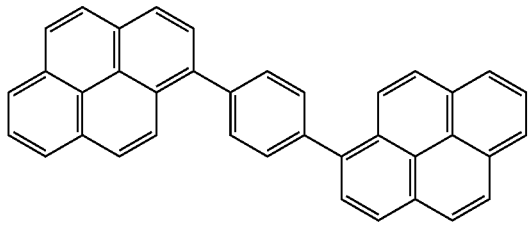

1-Bromopyrene (2.00 g, 7.12 mmol) was dissolved in anhydrous THF (150 ml) and anhydrous ether (150 ml). The light yellow solution was cooled to −78° C. in nitrogen. n-Butyllithium (4.9 ml, 7.83 mmol) was slowly dripped into the solution. At this time, the solution became murky. This mixture was kept at −78° C. for ten minutes, 0° C. for ten minutes, and then −78° C. for thirty minutes. Then, triisopropyl borate (4.93 ml, 21.36 mmol) was slowly dripped into the solution, and the mixture was kept at −78° C. for thirty minutes. Finally, the mixture underwent reaction at room temperature for 1.5 days. Next, water was added into the reaction mixture, and the resulting mixture was stirred vigorously for one hour. The water layer and the organic layer were separated, the water layer was then extracted by ethyl ether (2×25 ml), and the organic layer was water washed (2×50 ml). The combined organic solution was contact with $MgSO_4$ to remove water, then filtered, and concentrated on a rotary evaporator to obtain a pyreneboronic acid solid product.

20 mmol of pyreneboronic acid, 3.29 g (10.0 mmol) of 1,4-diiodobenzene, and 0.065 g (0.25 mmol) of $PdCl_2(CH_3CN)_2$ were placed in a 150 ml two-necked reaction bottle. Vacuum was developed in the reaction bottle then nitrogen was introduced into the reaction bottle, and this cycle was repeated a few times. 40 ml of DMF was introduced into the reaction bottle. The reaction temperature was raised to 50° C. for 18 hours to complete the reaction.

The reaction mixture was filtered with silica gel and diatomite, and was washed with dichloromethane. The combined filtrate was concentrated on a rotary evaporator, the resulting solid product was purified by separation with a silica gel column. The eluent used in a mixed solvent of ethyl acetate:hexane=1:5. After purification, 1.81 g of a pale yellow solid product 1,4-bipyrenylbenzene [IIb-1] was obtained with a yield of 80%.

Example 6~Example 20

Example 6~Example 20 are examples for the production of organic light emitting diodes. The organic light emitting diodes according to the present invention were all prepared according to the following procedure: A glass sheet was used as a substrate. The following elements were sequentially formed on the substrate: a positive electrode, a hole injection modification layer (optional), a hole transporting layer, a light emitting layer (wherein the hole transporting layer and the light emitting layer could be an identical layer), an electron transporting layer, and a negative electrode. The positive electrode was made of a conductive indium-tin-oxide (ITO) with a thickness of about 100 nm. Prior to the evaporation deposition of the organic layer, a commercial detergent and an organic solvent were used for cleaning the ITO glass. Finally, the product was processed with an UV-ozone cleaner.

The hole transporting layer could be made of a material selected from: NPB (4,4'-bis[N-(1-naphthyl-1-)-N-phenyl-amino]-biphenyl), TPD (1,4-bis[phenyl-m-tolyl]aminobiphenyl), m-MTDATA (4,4',4"-tris(3-methylphenylphenylamino)triphenylamine, and HT-2, which are shown in the following formulas:

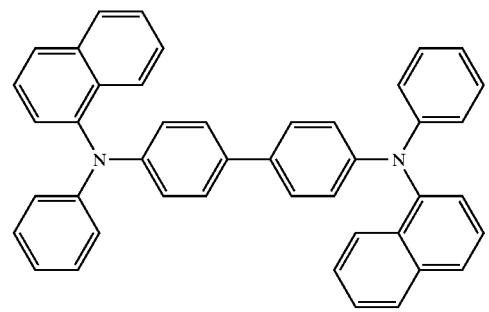

NPB

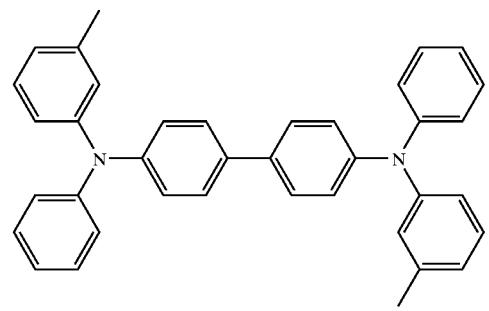

TPD

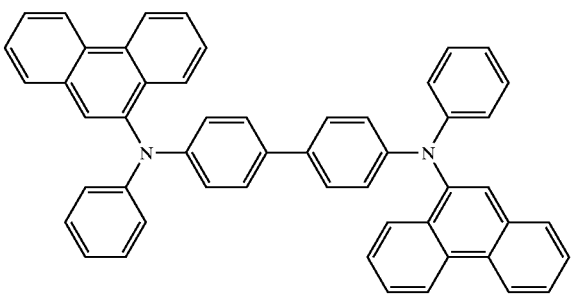

HT-2

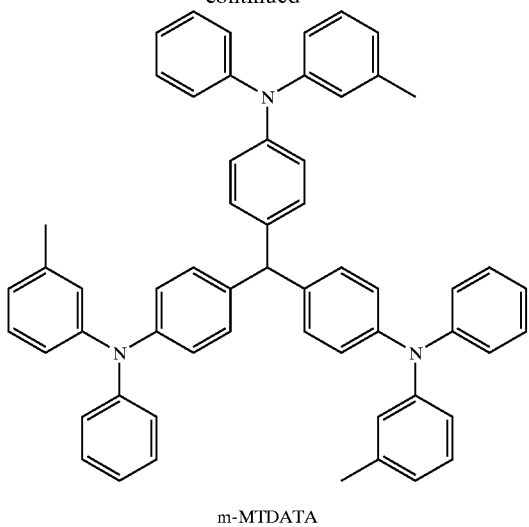

m-MTDATA

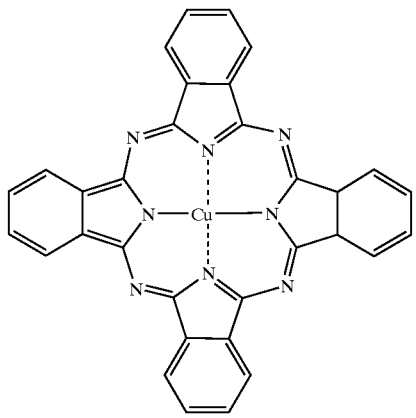

CuPc

The electron transporting layer could be made of a material selected from: Alq$_3$ and TPBI (2,2',2"-(1,3,5-benzenetriyl)tris-[1-phenyl-1H-benzimidazole]):

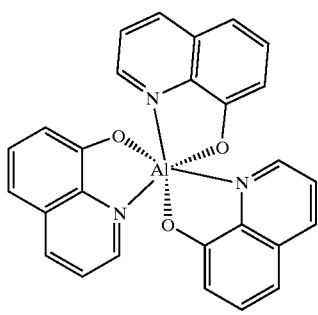

Alq$_3$

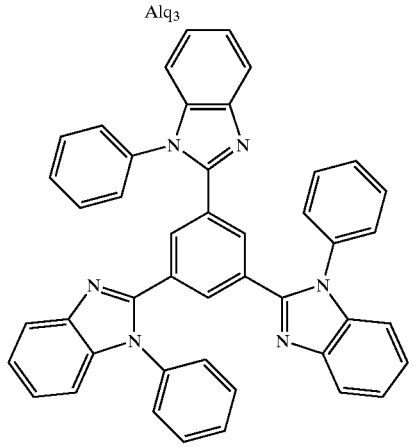

TPBI

The hole injection modification layer could be made of a material selected from: CuPc. m-MTDATA and 2-TNATA, which are shown in the following formulas:

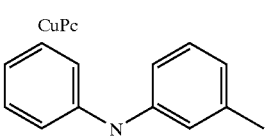

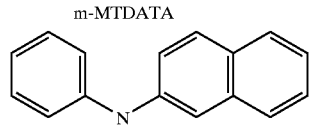

m-MTDATA

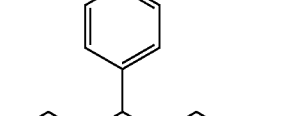

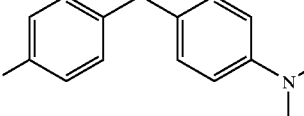

2-TNATA

During the production of the device, the evaporation of the organic material and CuPc used a chamber pressure of about $2\times10^{-6}$ torr and an evaporation rate of about 0.1–0.4 nm/s. The thickness of the hole injection modification layer was about 10 nm. The hole injection layer had a thickness of about 5–70 nm. The thickness of the electron transporting layer was 5–60 nm. The negative electrode was made of a Mg:Ag alloy (Mg:Ag=10:1), wherein the deposition rate for magnesium was 10 Å/s and 1 Å/s for silver, and the thickness thereof was 50–200 nm. Finally, a silver layer with a thickness of about 100 nm was plated as a protective layer. The performance of the devices fabricated in these examples were listed in Table 1; and the structures thereof were shown in the following:

Example 6

ITO/Ia-1 (40 nm)/Alq$_3$ (40 nm)/Mg:Ag=10:1

Example 7

ITO/CuPc (10 nm)/NPB (40 nm)/Ia-1 (40 nm)/Alq$_3$ (40 nm)/Mg:Ag=10:1

Example 8

ITO/CuPc (10 nm)/NPB (40 nm)/Ia-1 (40 nm)/ TPBI (20 nm)/Alq$_3$ (20 nm)/Mg:Ag=10:1

Example 9

ITO/m-MTDADA (10 nm)/NPB (40 nm)/Ia-1 (40 nm)/Alq$_3$ (40 nm).

Example 10

ITO/Ia-1 (40 nm)/TPBI (40 nm)/Mg:Ag=10:1

Example 11

ITO/CuPc (10 nm)/NPB (40 nm)/Ia-1 (40 nm)/ TPBI (40 nm)/Mg:Ag=10:1

Example 12

ITO/TPD (40 nm)/Ia-1 (20 nm)/TPBI (40 nm)

Example 13

ITO/IIb (30 nm)/Alq$_3$ (40 nm)/Mg:Ag=10:1

Example 14

ITO/CuPc (10 nm)/NPB (50 nm)/IIa-1 (30 nm)/ Alq$_3$ (40 nm)/Mg:Ag=10:1

Example 15

ITO/IIa-1 (30 nm)/TPBI (40 nm)/Mg:Ag=10:1

Example 16

ITO/CuPc (10 nm)/NPB (50 nm)/IIa-1 (30 nm)/ TPBI (40 nm)/Mg:Ag=10:1

Example 17

ITO/CuPc (10 nm)/TPD (50 nm)/IIa-1 (30 nm)/ TPBI (30 nm)/Mg:Ag=10:1

Example 18

ITO/CuPc (10 nm)/NPB (50 nm)/IIb-1 (30 nm)/ TPBI (40 nm)/Mg:Ag=10:1

Example 19

ITO/CuPc (10 nm)/NPB(50 nm)/Id-1 (30 nm)/TPBI (40 nm)/Mg:Ag=10:1

Example 20

ITO/CuPc (10 nm)/NPB (50 nm)/Ia-2 (30 nm)/ TPBI (40 nm)/Mg:Ag=10:1

TABLE 1

| Ex. | Brightness, cd/m$^2$ (volt) | Maximum efficiency, cd/A (volt) | CIE coordinate (x, y) (6 V) | Color of light |
|---|---|---|---|---|
| Ex.6 | 22321 (11.9) | 5.3 (8.5) | (0.25, 0.53) | green |
| Ex. 7 | 17839 (15.0) | 3.4 (10.0) | (0.16, 0.19) | blue |
| Ex. 8 | 15858 (14.5) | 2.7 (7.5) | (0.14, 0.09) | blue |
| Ex. 9 | 20474 (14.5) | 3.6 (9.5) | (0.16, 0.23) | blue |
| Ex. 10 | 5843 (13.5) | 1.2 (6.5) | (0.15, 0.07) | blue |
| Ex. 11 | 21215 (13.5) | 3.1 (6.0) | (0.15, 0.10) | blue |
| Ex. 12 | 26096 (13.5) | 4.1 (6.5) | (0.15, 0.12) | blue |
| Ex. 13 | 24221 (11.9) | 5.8 (8.4) | (0.25, 0.53) | green |
| Ex. 14 | 25638 (11.9) | 5.2 (8.9) | (0.15, 0.20) | blue |
| Ex. 15 | 17955 (11.4) | 2.7 (6.4) | (0.14, 0.14) | blue |
| Ex. 16 | 44507 (13.4) | 6.9 (7.9) | (0.14, 0.20) | blue |
| Ex. 17 | 32047 (11.4) | 4.2 (6.9) | (0.14, 0.19) | blue |
| Ex. 18 | 46306 (12.4) | 6.4 (6.4) | (0.17, 0.31) | blue green |
| Ex. 19 | 3220 (15.0) | 1.6 (8.0) | (0.15, 0.11) | blue |
| Ex. 20 | 3945 (12.0) | 1.1 (7.0) | (0.14, 0.11) | blue |

The data in Table 1 show that the blue-light emitting diodes fabricated according to the present invention have a high brightness, a high external quantum and current efficiency, and an excellent CIE coordinate.

What is claimed is:

1. An organic light emitting diode, which comprises: a positive electrode formed on a substrate; a negative electrode; and a light emitting layer disposed between said positive electrode and said negative electrode, wherein said light emitting layer comprises a compound having a formula Ia-1

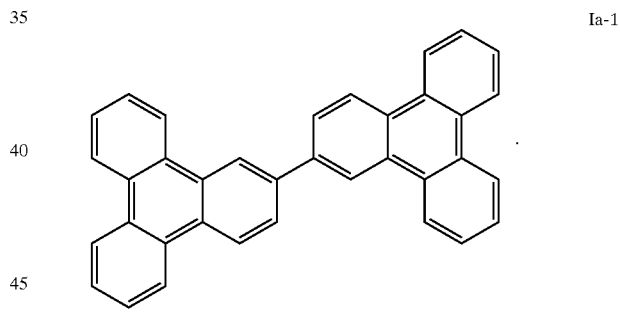

2. An organic light emitting diode as claimed in claim 1 further comprising an electron transporting layer formed between said light emitting layer and said negative electrode.

3. The organic light emitting diode as claimed in claim 2 further comprising a hole transporting layer formed between said positive electrode and said light emtting layer.

4. The organic light emitting diode as claimed in claim 2, wherein said light emitting layer is also a hole transporting layer.

5. The organic light emitting diode as claimed in claim 3 further comprising a hole injection modification layer formed between said positive electrode and said hole transporting layer.

6. The organic light emitting diode a claimed in claim 4 further comprising a hole injection modification layer formed between said positive electrode and said light emitting layer.

7. An organic light diode, which comprises: a postive electrode formed on a substrate; a negative electrode; and a light emitting layer disposed between said postive electrode and said negative electrode, wherein said light emitting layer comprises a compound having a formula

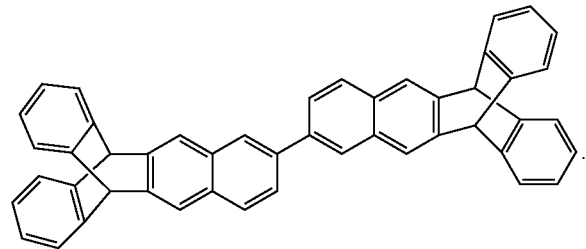

Id-1

8. The organic light emitting diode as claimed in claim 7 further comprising an electron transporting layer formed between said light emit ing layer and said negative electrode.

9. The organic light emitting diode as claimed in claim 8 further comprising a hole transporting layer formed between paid positive electrode and said light emitting layer.

10. The organic light emitting diode as claimed in claim 8, wherein said light emitting layer is also a hole transporting layer.

11. The organic light emitting diode as claimed in claim 9 further comprising a hole injection modification layer formed between said positive electrode and said hole transporting layer.

12. The organic light emitting diode as claimed in claim 10 further comprising a hole injection modification layer formed between said positive electrode and said light emitting layer.

* * * * *